United States Patent [19]

Oita et al.

[11] 4,065,576

[45] Dec. 27, 1977

[54] METHOD FOR USING A RUMINANT REPELLENT COMPRISING OXIDATION PRECURSORS OF ALIPHATIC ALDEHYDES

[75] Inventors: Katashi Oita; Marion R. San Clemente; John H. Oh; George T. Tiedeman, all of Seattle, Wash.

[73] Assignee: Weyerhaeuser Company, Tacoma, Wash.

[21] Appl. No.: 704,364

[22] Filed: July 12, 1976

Related U.S. Application Data

[63] Continuation-in-part of Ser. No. 502,003, Aug. 30, 1974, abandoned, which is a continuation-in-part of Ser. No. 291,059, Sept. 21, 1972, abandoned.

[51] Int. Cl.$^2$ ............................................. A01N 9/24
[52] U.S. Cl. ..................................... 424/318; 424/95; 424/312; 424/328; 424/333
[58] Field of Search ............................... 424/318, 312

[56] References Cited

U.S. PATENT DOCUMENTS 2,086,670   7/1937   Grimes ................................. 424/172

OTHER PUBLICATIONS

Chemical Abstracts J3:22718g (1959).
Lesser—Soap & Sanitary Chemicals, pp. 123–127 & 149–151 (1949).
Merck Index, 8th ed., pp. 763–764 (1968).

*Primary Examiner*—Leonard Schenkman
*Attorney, Agent, or Firm*—Christensen, O'Connor, Garrison & Havelka

[57] ABSTRACT

A method for discouraging ruminants from browsing edible material normally eaten by such ruminants comprises contacting the material and/or the region adjacent such material with a repellent composition. The repellent composition contains as the active repellent ingredient an aliphatic aldehyde, preferably having from six to 12 carbon atoms. The repellent composition can also be applied to the material as a repellent-producing composition that is an oxidation precursor of the aliphatic aldehyde.

8 Claims, No Drawings

METHOD FOR USING A RUMINANT REPELLENT COMPRISING OXIDATION PRECURSORS OF ALIPHATIC ALDEHYDES

BACKGROUND OF THE INVENTION

This application is a continuation-in-part of the patent application Ser. No. 502,003, filed Aug. 30, 1974, abandoned, which is in turn a continuation-in-part of the patent application Ser. No. 291,059, filed Sept. 21, 1972, now abandoned. The benefit of the filing dates of both of which are claimed under 35 USC 120.

The present invention relates to a method for treating material normally eaten by free roaming ruminant animals, or treating the area surrounding such material, to discourage such ruminants, for example members of the deer family, from browsing the edible material. More particularly, the present invention relates to a method for treating edible material with a specific class of ruminant repellent compositions comprising certain aldehydes and the oxidation precursors of these aldehydes.

In those agricultural industries which grow crops such as timber or food in regions adjacent to or within areas having a high ruminant animal population, the yearly loss of useful plant life to browsing or grazing by ruminants reaches staggering proportions. It has been estimated that the irreversible loss of timber resulting from ruminant browsing, either by stunting of growth or entirely killing trees, exceeds many millions of dollars per year. This loss is caused primarily by members of the deer family, which browse on timber producing trees, such as Douglas fir seedlings, during the late fall and winter seasons, and which selectively browse on the current growth of timber-producing trees in the spring and early summer seasons. The timber industry has been seeking a way to prevent such browsing by ruminants. A variety of compositions have been tried as ruminant repellents, but only a few have met with relative success.

Among those materials which have been effectively used as ruminant repellents are the putrefied products of a mixture of a lipoidal material and a lipolytic enzyme. One effective repellent composition has been derived from the putrefaction product of whole fish and lipolytic enzyme in excess of that present in the whole fish. Although these repellent compositions are effective, the putrefaction process is rather expensive, is extremely obnoxious to those who must work with it, meets with some ecological objections, and also produces some materials that may be phytotoxic, mammalian toxic or otherwise harmful to the ecosystem. A continuing search for effective, less toxic, and easier to handle ruminant repellents has culminated in the present invention.

It is a broad object of the present invention to provide a ruminant repellent that, alone or in combination with other repellent compositions, will effectively discourage browsing by ruminants of edible material such as trees. Further objects of the present invention are to provide an inexpensive, readily available ruminant repellent, to provide a ruminant repellent which is not derived from a putrefaction process, to provide a ruminant repellent that can easily be applied to edible material in unputrefied form, and to provide a ruminant repellent that is compatible with the forest ecosystem and especially that has little or no phytotoxicity or mammalian toxicity.

Other objects of the present invention are to provide a ruminant repellent that can be synthesized or that can be derived from natural sources and that can be applied to edible material in a relatively pure form to repel ruminants, to provide precursors for a ruminant repellent that, when applied to edible material, will produce active repellent ingredients over a relatively long period of time, to provide a ruminant repellent that can be applied to edible material in pure form or that can be mixed with other ingredients to control the release of the active repellent ingredient, and to provide compositions that, when applied to edible material in combination with another known repellent, will enhance the repellent effectiveness of the known repellent. Additional objects of the invention are to provide a broad range of hydrocarbon compounds that produce active repellent ingredients upon application to edible material, and more specifically, to provide a specific class of compounds that are especially suited to produce active repellent ingredients upon application to edible materials, and to provide a method for enhancing the effectiveness of the class of repellent-producing hydrocarbon compounds.

SUMMARY OF THE INVENTION

In accord with the foregoing objects, and other objects which will become apparent upon reading the following specification, the present invention provides a method for discouraging ruminants from browsing material normally eaten by such ruminants. The method comprises contacting the region adjacent to such material, or applying directly to such material, an amount of a repellent composition or repellent-producing composition effective to discourage browsing of the material by ruminants. The repellent composition contains as the active repellent ingredient unsaturated aliphatic hydrocarbons having the formula

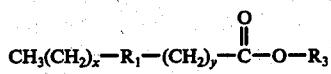

wherein $x$ is 5 through 7, inclusive, $y$ is 5 through 7, inclusive, $R_1$ is $-CH=CH-$ or $-CH=CH-CH=CH-$, $R_1$ having at least one cis carbon-carbon double bond, and wherein $R_3$ is hydrogen, an alkali or alkaline earth metal, an ammonium ion, an alkyl group having from one to six carbon atoms, or glyceryl. This repellent-producing ingredient is applied to the edible material under conditions that allow the ingredient to undergo autoxidation to an aliphatic aldehyde by cleavage of the hydrocarbon chain at or near the unsaturated bond.

DESCRIPTION OF PREFERRED EMBODIMENTS

Description of Terms

The following paragraphs define certain of the terms utilized in the present specification. These definitions are not intended to be exclusive, but are intended to be used as a guide to one of ordinary skill in the art in understanding, making and using the invention. The term "repellent" or "repellent composition" as used herein is a composition of matter, including mixtures, which effectively repels or discourages animals from foraging or browsing upon edible material. The term "edible materials" is used herein primarily to refer to plant or vegetable matter that is normally eaten and digested by animals. Examples of edible materials include the leaves of trees upon which ruminants normally browse. The term "leaf" or "leaves" includes the needles of coniferous trees. The term "ruminant" includes those animals such as deer, elk and members of the bovine species which have a ruminal digestion. A "ruminant repellent" according to the present invention is a composition of matter which effectively discourages browsing by ruminants upon edible material to which the repellent has been applied. The term "browsing" as used herein means the effective removal of all or part of the leaf, twig, branch or other part of living plant matter, or the biting into of other edible material. For purposes of the examples and the bioassay procedures set forth below, a leaf is considered browsed even if it is merely nipped from a branch or from its location in one of the tests and is thereafter deposited on the ground, but not wholly eaten by the animal. The term "repellent-producing composition" is utilized to refer to materials which before or after application to edible material will undergo a chemical change to yield an active repellent ingredient.

The term "oxidation" as used herein refers to the chemical reaction wherein an unsaturated hydrocarbon group is attacked by oxygen to yield oxygenated intermediate reaction products that ultimately cleave at or near the carbon-carbon double or triple bond to yield an aldehyde. Oxidation occurs when free oxygen or oxygen combined in suitable organic oxidizing agents attacks the hydrocarbon group. The term "autoxidation" refers to oxidation which occurs upon exposure to air, and preferably to sunlight, at ordinarily encountered atmospheric temperatures, e.g., from $-35°$ C. up to $50°$ C.

The term "carrier" is used to define a composition or mixture of materials which may be used to dilute a repellent or repellent-producing composition to enhance the application characteristics of the composition. Water and both water immiscible and water miscible solvents for the repellent and repellent producing compositions can be used as carriers. The term "formulate" is utilized herein to define the process by which the repellent or repellent-producing composition is combined and/or suspended in a carrier. "Formulation" defines the composition of matter resulting from formulating a repellent or repellent-producing composition. The term "contacting" is used in the context of applying the repellent or repellent-producing composition or formulation to edible material and is used to define the process step by which the composition is deposited on the edible material or is caused to come into intimate contact with the edible material. The term "applying" is used interchangeably with the term "contacting."

The term "unputrefied" is used herein to describe a material that has not been subjected to the putrefaction process to any substantial extent, i.e., that a material capable of putrefaction has not become putrefied or decomposed to the extent that the material has produced decomposition products which are toxic to animals. The term "putrefied" is used to describe a material that has been subjected to the chemical reaction normally known as putrefaction, which occurs when a lipoidal and/or proteinaceous material undergoes an essentially uncontrolled microbiological decomposition. The products of a controlled fermentation process would be unputrefied within the meaning intended herein.

DESCRIPTION OF EMBODIMENTS

Aliphatic aldehydes are effective ruminant repellents when applied to edible material. When present on edible material, members of this broad class of aldehydes will volatilize to varying degrees depending upon the volatility characteristics of the particular aldehyde and depending upon the ambient conditions surrounding the edible material. When ruminants approach the vicinity of the volatilized aldehydes, they are discouraged from browsing upon the edible material. Whether the repellent effect of the aldehydes is due to an olfactory sense or other sense is not known. What is known is that, when one of the members of this class of aldehydes is applied to edible material, it is effective to prevent ruminants from browsing upon, or in most instances, even reaching the proximity of the edible material.

All of the aliphatic aldehydes that are to any degree volatile under normal atmospheric conditions, whether saturated or unsaturated, are effective to repel ruminants. The aldehydes of intermediate molecular weight are most effective since their volatility is relatively low, i.e., they do not evaporate within a very short time after application to the edible material. The lower aliphatic aldehydes, those having from one to five carbon atoms, are highly volatile compounds. Although the lower aliphatic aldehydes will effectively repel deer, they are not preferred since they quickly volatilize and disappear from the edible material, causing the repellent effect to be very short-lived. The aliphatic aldehydes that have more than 12 carbon atoms have a limited effectiveness as ruminant repellents as they do not tend to volatilize quickly under normal atmospheric temperatures. However, for this reason they can be used during very hot weather as they will volatilize sufficiently to be effective to prevnt browsing by ruminants. Thus the aliphatic aldehydes having from six to 12 carbon atoms, which are of intermediate volatility, are preferred for most commercial applications. The most effective aliphatic aldehydes under generally prevailing atmospheric conditions (from $-5°$ to $30°$ C.) are those having from eight to 11 carbon atoms.

These aliphatic aldehydes can be purchased commercially and applied directly to edible material. However, the aldehydes are subject to autoxidation under normal atmospheric conditions to yield acids and other oxidation products. When the aldehydes are oxidized, their effectiveness as a ruminant repellent is destroyed. Thus, an application system in which the aldehydes are continuously produced and/or allowed to volatilize over a long period of time is necessary to prolong the repellent effect.

The aliphatic aldehydes can be produced by autoxidation of many compounds, primarily relatively long chain unsaturated aliphatic hydrocarbons. These compounds can be applied directly to edible material and allowed to autoxidize to yield the active repellent ingredients. The unsaturated hydrocarbon compounds are preferred for direct application to edible material since a hydrocarbon chain containing the unsaturated carbon-carbon bond is readily attacked by oxygen. A small amount of unsaturated hydrocarbon is capable of undergoing autoxidation to produce an effective repellent over a relatively long period of time, on the order of from 4 to 8 weeks or longer. Saturated hydrocarbons can be oxidized under extreme oxidizing conditions to yield a certain amount of the aldehydes that are effective ruminant repellents. However, the autoxidation of saturated hydrocarbons is relatively slow when compared to unsaturated compounds, and thus saturated compounds will not produce an effective amount of the active repellent ingredient under normally encountered atmospheric conditions.

The unsaturated aliphatic hydrocarbons, defined more completely below, are referred to herein as the oxidation precursors of the aliphatic aldehydes. Although the aliphatic aldehydes are presently believed to be the active repellent ingredient that, upon volatilizing from the edible material, repels ruminants and discourages them from browsing upon the edible material, the short-lived, intermediate reaction products, which are produced upon oxidative degradation of the unsaturated aliphatic hydrocarbons to the aliphatic aldehydes, may also be active repellent ingredients.

A broad class of unsaturated aliphatic hydrocarbons that will yield the aldehydes upon oxidation are broadly defined by the formula

wherein $R_1$ is $-CH=CH-$ or $-C\equiv C-$, $R_2$ is a straight or branched chain alkyl, alkenyl, or alkynyl group having from 5 to 11 carbon atoms, and $R_3$ is hydrogen or a substituted or unsubstituted hydrocarbon group, the total number of carbon atoms in the unsaturated aliphatic hydrocarbon being less than 25. Hydrocarbon compounds having the foregoing formula wherein $R_2$ and $R_1$ are similarly defined and wherein $R_3$ is an aliphatic, alicyclic, or aromatic group are also effective as repellents. These compounds, when applied directly to edible material as the principal repellent-producing ingredient, must be applied under reaction conditions that allow the ingredient to undergo autoxidation to an aliphatic aldehyde, i.e., effective oxidation inhibitors cannot be present. Under such conditions these unsaturated aliphatic hydrocarbons produce a large proportion of aldehydes having from 6 to 12 carbon atoms that are effective to discourage browsing of edible material by ruminants when applied to edible material. Since the aldehydes having from 6 to 12 carbon atoms are preferred for the reasons given above, it is preferred that the unsaturated aliphatic hydrocarbon precursor include an $R_3$ radical having from 5 to 11 carbon atoms. Best results are obtained with an unsaturated aliphatic hydrocarbon having a total number of carbon atoms in the range of 16 to 20, inclusive. To yield the aliphatic aldehydes that are effective under the normally encountered atmospheric conditions, the unsaturated bond must occur somewhere between the fifth and the 12th carbon atom in the hydrocarbon chain, since the oxidative cleavage is selective to the unsaturated bond or the carbon-carbon bonds adjacent or next adjacent to the unsaturated bond. Upon oxidative cleavage of an unsaturated bond in one or more of these positions, at least one aldehyde of the preferred class is produced, although two or more aldehydes may be produced dependent upon the other functional groups present in the aliphatic hydrocarbon chain. When $R_3$ contains at least five carbon atoms, the possibility that two of the preferred aldehyde molecules will be produced from autoxidation of a single hydrocarbon molecule is greatly increased. Examples of compounds falling within the foregoing class of compounds, which upon application to edible material have exhibited effective repellency are linoleic, linolenic, oleic, erucic, vaccenic, brassidic and elaidic acids.

Among the broad class of unsaturated aliphatic hydrocarbons that yield effective repellent compositions upon oxidation is a specific class of compounds that is especially susceptible to autoxidative production of aldehydes having from 8 to 11 carbon atoms. This specific class of compounds includes oleic acid, compounds related to oleic acid, cis-9-octadecene, and cis-9-octadecene-1-ol, linoleic acid and linolenic acid. This specific class of compounds is best defined by the formula

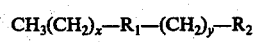

wherein $x$ is 5 through 7, inclusive, $y$ is 5 through 7, inclusive, $R_1$ is $-CH=CH-$ or $-CH=CH-CH=CH-$, $R_1$ having at least one cis carbon-carbon double bond, and $R_2$ is

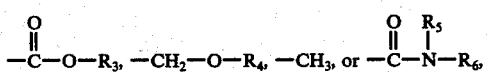

wherein $R_3$ is hydrogen, an alkali or alkaline earth metal ion, an ammonium ion, an alkyl group having from one to six carbon atoms, gyceryl or

$R_4$ is hydrogen, an alkyl group having from one to six carbon atoms, or

$R_5$ and $R_6$ are independently selected from hydrogen or an alkyl group having from one to six carbon atoms, and $R_7$ is an alkyl group having from one to five carbon atoms. These repellent-producing compounds must also be applied to the edible material under reaction conditions that will allow at least a portion of the repellent-producing ingredient to undergo autoxidation to an aliphatic aldehyde. Because of the location of the carbon-carbon double bond in this class of compounds, a large proportion of the most effective aldehydes having from 8 to 11 carbon atoms are produced.

Among the intermediate class of compounds enumerated in the preceding paragraph, the acid derivatives wherein $R_2$ is

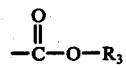

are preferred because of ready availability on the commercial market and because these compounds readily autoxidize to the aldehyde after application. Within the class of compounds $R_3$ can be any group that will allow the compound to undergo autoxidation, that is, will not interfere with or retard autoxidation of the compound, at locations at or adjacent a carbon-carbon double bond in the $R_1$ group. The most preferred $R_3$ groups within the purview of the invention are those specifically enumerated in the preceding paragraph.

When the term "glyceryl" is used herein it is intended to encompass only the following chemical entities: 1,2-diacyloxypropyl; 1,3-diacyloxypropyl; 1-acyloxy -2-hydroxypropyl; 2-acyloxy-1-hydroxypropyl; 1,2-dihydroxypropyl; or 1,3-dihydroxypropyl; wherein the acyl portions of the glyceryl groups are derived from linear, aliphatic or olefinic carboxylic acids that have from 14 to 20 carbon atoms.

Within the preferred class of unsaturated aliphatic hydrocarbons defined immediately above, those having the carbon-carbon double bond at the nine position in the hydrocarbon chain are most preferred. The compounds having a carbon-carbon triple bond are a less preferred form of the unsaturated aliphatic hydrocarbon, as the triple bond is highly reactive, and thus susceptible to reactions that will either too rapidly form aldehydes or will simultaneously undergo side reactions to produce products which are not effective repellents. The cis carbon-carbon double bond is most preferred as those compounds that contain it are more susceptible to the desired oxidative reaction than are those compounds containing trans carbon-carbon double bond. Within this most preferred class of unsaturated aliphatic hydrocarbons, oleic acid and the ammonium, alkali and alkaline earth metal salts of oleic acid, the lower esters of oleic acid, and the fatty acid glycerides wherein at least one of the fatty acids is oleic acid are preferred from the commercial standpoint since they are readily available, are relatively inexpensive, are easily formulated, and exhibit little or no phytotoxicity or mammalian toxicity.

It should be understood that the oxidation precursors to the effective repellents, the aliphatic aldehydes, are not repellent in and of themselves, but must be allowed to undergo at least some oxidation before they will function to produce effective repellents. Thus if chemically pure compounds such as a glyceride of oleic acid are applied to leaves, they may not be immediately effective to prevent browsing of the leaves, but will require some period of time to oxidize to the aldehydes. For example, exposing a glyceride of oleic acid to direct sunlight before or after application to the leaves will cause sufficient autoxidation to yield an effective repellent composition. Therefore, if immediate repellency is desired, a commercial grade of, for example, a glyceride of oleic acid is preferred for application since the commercial grade material has undergone sufficient autoxidation to produce an adequate quantity of aldehydes to function as an effective ruminant repellent.

Not only can the foregoing ruminant repellent compositions and repellent-producing compositions be employed effectively as the principal active repellent ingredient, these compositions can also be used to fortify other known repellents, such as the putrefied lipoidal materials mentioned above, to enhance the repellent effectiveness of the known repellents. For this use oleic acid and its salts are preferred. The repellent and repellent-producing compositions of the present invention can also be used in combination with repellents not specifically effective on ruminants, for example, rabbit repellents such as tetramethylthiuram disulfide, commercially available from E. I. duPont de Nemours and Company under the trade name "Arasan."

The repellent-producing precursor compositions can also be pre-oxidized by combining the compositions with an oxidizing agent or a source of oxygen prior to application of the precursors to edible material. To enhance the effectiveness of a given precursor, the pre-oxidation should be carried to an extent that will cause the precursors to undergo limited oxidation to produce intermediate oxidation products that react to the aldehydes and to produce the aldehydes in limited quantity. This technique enhances the immediate repellent activity of a given precursor and is especially efficacious with long chain saturated aliphatic hydrocarbons as well as the unsaturated hydrocarbons set forth above. In addition, the readily available source of oxygen after application will allow the precursors to oxidize to the aldehydes more quickly, thus providing a stronger repellent effectiveness per unit of repellent-producing ingredient applied to the edible material. With the broad class of precursors, an excellent yield of aldehydes having from six to 12 carbon atoms can be obtained upon pre-oxidation. When the precursors having 18 carbon atoms with a cis double bond at the 9 position are pre-oxidized, an abundance of the aldehydes having from 8 to 11 carbon atoms are produced. Moreover, oxidation catalysts can be combined with the repellent-producing precursors to provide even greater yields of the active repellent ingredients. Examples of such catalysts and oxygen sources are spray dried animal blood, potassium permanganate and other oxidizing agents. A good yield of the aldehydes can be initiated by heating the repellent-producing precursors to temperatures above the normally prevailing ambient temperatures. For example dried animal blood and oleic acid can be combined in an approximate 1:10 ratio respectively and heated to about 50° C. while thoroughly continuously mixing the two components with air. If this oxidation process is continued for a period of 11 days, the repellent activity of the resulting product is enhanced. The repellent effectiveness of the precursors can also be enhanced by subjecting the precursors to other reaction conditions known to promote oxidation. For example, heating in a closed vessel in the presence of limited quantities of oxygen carried on at temperatures on the order of 100° to 200° C. will significantly enhance the yield of active repellent ingredients.

The repellent compositions, including both the aldehydes and the repellent-producing oxidation precursors, can be applied directly to edible material. It is preferred for commercial application that the repellent compositions be combined with a carrier and a binder. The binder causes the active repellent composition to adhere to edible material. Both aqueous and nonaqueous carriers can be employed. It may also be necessary to employ an emulsifying agent to assure a thorough intermixture of the repellent composition when using an aqueous carrier. One effective repellent formulation which can be sprayed on edible material is formed by combining the repellent composition with a binder, an emulsiying agent, if necessary, and water in relative amounts ranging from 0.1 to 10% of the repellent composition, from 10 to 20% of the binder, and from 70 to 89.9% of water. A preferred aqueous formulation for the active repellent ingredient, i.e., the aldehydes contains about 0.3% of the repellent composition, 13.5% binder and 86.2% water. The preferred formulation for the repellent-producing composition, i.e., the precursors to the aldehydes, contains about 1.5% of the repellent composition, 13.5% binder and 85% water. The foregoing percentages and all other percentages given herein are by weight based on the total mixture unless otherwise designated.

A suitable binder which also serves as an emulsifying agent is "UCAR 180," an acrylic vinylacetate, nonionic emulsion copolymer containing a nonionic emulsifier. "UCAR 180" is a tradename of and is available from the Union Carbide Company. Another binder, "Raeco No. 780 RB" having an asphaltic base is also effective.

"Raeco No. 780 RB" is a tradename for an emulsified asphaltic base carrier containing at least about 56% by weight of asphalt solids in water. It is available from Raeco Products Company, 5700 Corson Ave., S., Seattle, Wash.

The binder can also be chosen from any of a large number of commercially available binders and emulsifiers, such as "Rhoplex AC 33," a tradename of the Rohm and Haas Company, Philadelphia, PA for its aqueous dispersions of acrylic copolymers; "Acryloid F-10," a tradename of the Rohm and Hass Company for its acrylic ester polymers in a mineral spirits solvent. ("Acryloid F-10" contains about 40% by weight of solid polymer); and "Carb-O-Set," an acrylic copolymer containing a precise ratio of polar carboxyl groups and nonpolar groups, available from B. F. Goodrich Chemical Company, Cleveland, Ohio (Carb-O-Set 514H is an aqueous solution and Carb-O-Set 514A is a solution of the co-polymer in a solvent such as isopropanol). Suitable binders and emulsifiers should not be phytotoxic, should set up relatively rapidly to aid the active ingredient in readily adhering to the plant, and should be relatively versatile with respect to the ambient conditions under which it can be applied.

Although aqueous carriers are used with great effectiveness for the repellent composition of the present invention, an initial preformulation can be made by combining the repellent composition with a water miscible solvent to form a repellent concentrate. In addition, a binder can be added for the same purposes as in the aqueous formulations above, i.e., to provide better adherence of the repellent composition to the edible material after application. This repellent concentrate contains all the requisite active ingredients and contains all the ingredients necessary to provide a commercially usable and effective ruminant repellent. This concentrate can then be further diluted with the same water miscible solvent and applied directly to edible material. If desired, the repellent concentrate can also be effectively and economically diluted with water for application to edible material. When the concentrate is combined with binders which are only partially miscible with water and when the concentrate is to be further diluted with water, it may be desirable, or necessary depending upon the nature of the binder system being utilized, to add a solubilizing agent such as ammonium hydroxide to form a more solubilized system.

Although preformulation with a water miscible solvent provides a more versatile repellent concentrate, any suitable solvent for the repellent composition can be employed to form the concentrate. If a water immiscible solvent is chosen, then dilution of the concentrate must be accomplished with the same solvent or a solvent which is miscible with the initially chosen water immiscible solvent. A suitable water immiscible solvent is "Chevron 250," a tradename of the Chevron Chemical Company, San Francisco, Calif., for its organic solvent comprising about 94% by weight of paraffins and napthenes and about 6% by weight of toluene.

Water miscible solvents which can be utilized to form a repellent concentrate are abundant. One group of water miscible solvents are the alkyl alcohols having from one to four carbon atoms. Other solvents which can be utilized and which exhibit the same low toxicity characteristics are exemplified by diacetone alcohol, dichloroethyl ether, dioxane, cellosolve (a tradename of the Union Carbide Company for its ethylene glycol monoethylether solvent), methyl ethyl ketone, and isopropyl acetate. Other effective but less preferred solvents, which may exhibit greater phytoxicity or mammilian toxicity than the foregoing, are disclosed in an article by Gast, R., and Early, J., *Agricultural Chemicals*, 10, April, 42(1956), pp 42, 43, 136, 137 and 139, expressly incorporated herein by reference. All of the solvents listed in the foregoing article which are water miscible will form an effective solvent for the repellent composition of the present invention. However, as can be seen from the data provided in the reference pages, several of the solvents have a relatively high phytoxicity, and thus are not desirable from that standpoint. Characteristics of the solvent which are desirable for a commercial, sprayable repellent composition include ready biodegradability without leaving toxic residue, water solubility for most applications, and a capability to solubilize the repellent composition. If a nonaqueous formulation is desired certain of the listed solvents which are not desirable from the water miscibility standpoint, such as ethylacetate and ethylene dichloride, can be employed.

The repellent formulations (both the aqueous and nonaqueous formulations thereof described above) can be applied to 2 and 3 year old Douglas fir seedlings, by conventional mechanical spraying apparatus. These formulations provide effective repellent properties when applied at the rate of 100 gallons of repellent formulation per 300,000, 2 year old seedlings and 100 gallons per 100,000 3 year old seedlings. As another example, where seedlings are planted at a density of on the order of 600 to 700 trees per acre, 1 to 2 gallons per acre applied by hand-held sprayers can be utilized to effectively prevent browsing of new growth on such trees by ruminants. The same formulation has also been found effective when sprayed in concentrations of about 10 gallons per acre from a helicopter. The foregoing application levels of the repellent compositions and formulations are intended to be representative of effective levels of repellency. One of ordinary skill after reading the foregoing specification will be able to adjust these effective application levels depending on the type of crop, the weather conditions, terrain, ruminant population, and other variables known to him.

The repellent compositions (both the aqueous and nonaqueous formulations thereof described above) are also effective to discourage ruminants from browsing edible material even if not directly applied to the edible material. Ruminants are repelled from an area or region to which they would otherwise normally be attracted because of the presence of edible material, if the ruminants encounter the presence of the repellent composition at the periphery of the area. When ruminants encounter the repellent at the periphery, they will tend not to cross the periphery into the area or region containing edible material. This holds true whether the area is relatively large, as a tree nursery or plantation, or small, as an area of several square feet containing a single 4 year old tree.

The repellent composition, formulated as described above, can be applied to the periphery of the area in several ways. The foliage and/or the land along the peripheral portion of the area can be sprayed in a 2 or 3 foot wide or wider strip, which strip surrounds the area from which is it desired to repel ruminants. Alternatively, a "chemical fence" can be prepared to repel ruminants from a chosen area. To prepare such a fence the repellent composition is sprayed onto, spread onto, or absorbed in a piece of material, such as a length of fiber rope, which in and of itself has no repellent effect, i.e., is relatively inert. The rope or other material is then placed along the peripheral portion of the area from which it is desired to repel ruminants. As ruminants encounter the strip surrounding the area, or the rope placed around the area, they are repelled, preventing them from gaining access to the area, and thus discouraging them from browsing any edible material which may be present in the area. Although any suitable type of material can be used as the substrate for the chemical fence, it is preferred that the material be of a nature which will retain effective amounts of the repellent composition. Thus, a natural fiber rope having good absorbent properties is desirable. The rope can be treated with the repellent composition by soaking it for a few hours in one of the foregoing repellent formulations. Thereafter, it can be strung along posts surrounding the area from which it is desired to repel ruminants.

In a like manner, the repellent formulations of the present invention can be used to divert ruminants from normal migration or range paths to guide them away from areas through which they might otherwise normally travel on a day-to-day or on a seasonal basis. For example, a strip several feed wide along a well traveled ruminant migration or range path can be sprayed with the repellent composition. The path of the sprayed strip can be located to cross over the normal migration path and lead into an area away from the region from which it is desired to repel the ruminants. As the ruminants travel their normal migration paths and encounter the strip sprayed with the repellent formulation, they will tend not to cross the strip and will instead be diverted along the side of the sprayed strip in a direction away from the region from which it is desired to repel them.

BIOASSAY TEST PROCEDURES

The products produced in the following examples were bioassayed on deer according to the bioassay test procedures described below. For purposes of both bioassay test procedures, the percent of leaves browsed was determined by dividing the number of leaves in the original test sample into the number of leaves browsed and multiplying by 100 percent. In each series of tests the product tested was compared with a treated control. For purposes of the comparisons in Table I, the treated controls were the products of Examples I and II. In both bioassay test procedures, the treated leaves were dipped in a formulation containing the repellent product produced in accord with the following examples. The binder and/or carrier used was "UCAR 180" and water, mineral oil, or a mixture of mineral oil and hexane unless otherwise noted. These binder and/or carrier systems alone have negligible repellent effectiveness.

Although neither of the test procedures utilized coniferous trees as edible test samples, the results can be directly correlated to results on Douglas fir and similar trees. Among other reasons, the edible samples used in the test procedures were chosen because of ease of identifying browsed samples and deer diet preferences corresponding to seasonal changes. Adequate feed for the deer was maintained in the pens in addition to the test samples. This feed normally took the form of a pelletized feed supplement and loose alfalfa in self-feeding troughs.

Care must be taken when interpreting the results of the bioassays. From test to test the browsing pressure can vary significantly, depending on the kind and relative availability of food other than the material used in the bioassay. The browsing habits of deer, as well as their preference for certain kinds of edible material including that used in the bioassays, change from week to week, and especially from season to season. These factors can cause significant variance among the browse readings if an attempt is made to compare one set of results with another set of results. The bioassay results set forth herein should only be used as an indication of the relative effectiveness of a given repellent sample. Although the effectiveness of some of the repellent samples is relatively short-lived, the results confirm the effectiveness of the repellent ingredient. It has been found that a repellent composition when applied in the field, as opposed to a closed test pen, is effective over a much greater time than indicated by the bioassay test results.

Test Procedure "H"

A madrone or black oak branch containing several sub-branches and having in total approximately 100 to 500 leaves was selected as the edible material. A sub-branch containing at least 10 succulent leaves was chosen as the test sub-branch to be treated. The leaves were counted and tagged. A second sub-branch separated from the first treated sub-branch containing at least 10 leaves was chosen as a control. Then leaves were counted on this branch and were tagged so that they could be counted if later browsed or eaten. The 10 leaves to be treated were dipped in or sprayed with the repellent formulation being tested. Great care was taken to prevent contamination of the untreated leaves, not only of the control but all the untreated leaves surrounding the treated sample.

The branches having treated leaves were placed in each of four adjacent pens, each containing the same number of deer. The number of deer in the pens as well as the maturity and sex varied among the several tests. The tests were duplicated in each pen and run at the same time. The results from the four pens were averaged to give the results in Table I. The tests were conducted until 100% of the untreated control was browsed.

Bioassay Procedure "T"

A herd of about 30 blacktail deer was penned in a 6 acre tract which is subdivided into a northern half and a southern half by an open-ended fence. The deer had free access to all 6 acres. About three-fourths of the pen had a cover of grasses and broad-leafed forbes and about one-quarter of the pen had trees, mostly Douglas fir, some maple, hazelnut, cedar, and true fir. The deer had constant access to harvested alfalfa hay, a specially formulated pelletized feed (containing salt), and running water.

The edible material used for the tests was branches of salal (*Gaultheria shallon*) which is readily browsed by wild deer during the 6 winter months from mid-October to mid-March, inclusive. The salal was prepared so that each branch bore 10 leaves. The branches were treated with a repellent composition by spreading about 0.125 grams of a repellent formulation, including repellent composition, binder and/or carrier on the upper side of each leaf and the same amount on the underside of the leaf.

Wooden 2 by 2 inch stakes were driven into the ground in rows in selected areas in the deer pen. The rows each contained about 13 stakes at 3 foot intervals with a second parallel row at a distance of 8 feet from the first row. This arrangement was replicated in both halves of the pen. Salal branches were attached to each of the stakes in sets of two, each set containing a pair of marked salal branches. One of each pair of the branches was untreated and served as a control while the other branch of each of the pairs was a treated sample.

After all the branches were attached to the stakes, the deer were given free access to the stakes and were allowed to browse the salal leaves at will. In a typical test 40 to 80 leaves were treated with the same composition. Browse readings were taken at intervals and averaged to provide a percentage browsed for the treated branches and a percentage browsed for the control branches. The browse counts were taken at various intervals depending on the browsing pressure and the life expectancy of the repellent compositions under test.

EXAMPLES

The following examples are intended to be illustrative and typical of the present invention and are not intended in any way to be delimitative. The examples are intended to assist one of ordinary skill in the art in making and using the invention disclosed herein. The weight percentages used in the following examples are calculated on the basis of the weight of the total formulation.

EXAMPLE I

Commercial oleic acid was formulated with a binder and water in the following proportions: oleic acid, 1.5% by weight; binder ("UCAR-180," identified above), 13.5% by weight; and water, 85% by weight. The commercial oleic acid was 76% oleic acid mixed with other acids and related products, and was sold under the tradename "NEO-FAT 94-04" by Armour Industrial Chemical Company, Chicago, Ill. The formulation was bioassayed in accordance with test procedure "H" outlined above. After 24 hours 100% of the untreated control leaves were browsed, when only 8% of those treated leaves were browsed. These bioassay results show that the formulation containing oleic acid was repellent, i.e., it prevented deer from substantially browsing the treated edible material.

EXAMPLE II

The procedure of Example I was repeated upon bioassay in accordance with test procedure "H" outlined above. After 24 hours none of the treated material was browsed when 100% of the untreated control leaves were browsed.

EXAMPLE III

Laboratory grade oleic acid (99% pure) was formulated with a carrier in the following proportions: oleic acid, 0.3% by weight; and carrier (a mixture of 15% by weight mineral oil and 85% by weight hexane), 99.7% by weight. The formulation was bioassayed in accordance with the test procedure "T" outlined above. One hour after application, 28% of the treated leaves as contrasted with 50% of the untreated control leaves were browsed. After 3 hours, 93% of the treated leaves were browsed as contrasted with 100% of the untreated control leaves. The results of this bioassay show that although the essentially pure oleic acid exhibits repellency, it is not as effective as a repellent as the commercial oleic acid that contains oxidative degradation products of oleic acid.

EXAMPLE IV

Laboratory grade oleic acid (99% pure) was placed in an open beaker exposed to the air under a mercury arc lamp for 16 hours at room temperature, during which time it was stirred continuously. The exposure to the mercury arc causes the laboratory ultraviolet light catalyzed oxidation with oxygen present in the air. The oxidation product was mixed with a carrier in the following proportions: product, 0.3% by weight; and carrier (a mixture of 15% mineral oil and 85% hexane), 99.7% by weight. The resulting formulation was bioassayed in accordance with test procedure "T" outlined above. After 1 hour, 5% of the treated leaves were browsed as contrasted with 23% of the untreated control leaves. After 3 hours, 95% of the treated leaves were browsed as contrasted with 100% of the untreated control leaves. The results of this bioassay show an improvement in the repellency when laboratory grade oleic acid is caused to undergo ultraviolet catalyzed oxidation.

EXAMPLE V cis-9-octadecene was bioassayed in accordance with the test procedure "T" outlined above. The cis-9-octadecene is prepared in accordance with the procedure outlined by Dyan, M. E. Hamann, H. C., and Swern, D. J., *Am. Oil Chemists'* 43, 431–2 (1966). No carrier or binder was used. After 2 hours, 48% of the treated leaves were browsed as contrasted with 93% of the untreated control leaves. After 4 hours, 50% of the treated control leaves were browsed as contrasted with 100% of the untreated control leaves.

EXAMPLE VI cis-9-octadecene was placed in a open beaker exposed to the air under a mercury arc lamp at room temperature for a period of 16 hours, during which time it was continuously stirred. The oxidation product was formulated in the following proportions: product, 0.3% by weight; carrier (mineral oil), 99.7% by weight. The formulation was bioassayed in accordance with test procedure "T" outlined above. After 2 hours and 4 hours, respectively, 0% of the treated leaves were browsed as contrasted with 38% of the untreated control leaves. After 6 hours, 18% of the treated leaves were browsed as contrasted with 93% of the untreated control leaves. After 8 hours, 28% of the treated leaves were browsed as contrasted with 98% of the untreated control leaves. And after 10 hours 68% of the treated leaves were browsed as contrasted with 100% of the untreated control leaves. The results of the bioassay illustrate that a singly unsaturated long chain alkene, when caused to undergo ultraviolet catalyzed oxidation, will provide an excellent repellent ingredient.

EXAMPLE VII

The procedure of Example VI is repeated with the additional step that prior to formulation, the autoxidation product is steam distilled by bubbling steam through the oxidation product container and trapping and condensing the vapors which distill over from the oxidized product. The steam distillation is continued for a period of about 2 hours. The residue left in the oxidation container is referred to as the non-steam volatile (NSV) fraction. The NSV fraction is formulated in the following proportions: NSV fraction, 0.3% by weight; and carrier (mineral oil), 99.7% by weight. The formulation was bioassayed in accordance with the test procedure "T" outlined above. After 2 hours, 25% of the treated leaves were browsed as contrasted with 88% of the untreated control leaves. After 4 hours 25% of the treated leaves were browsed as contrasted with 88% of the untreated control leaves. And after 6 hours, 48% of the treated leaves were browsed as contrasted with 100% of the untreated control leaves.

EXAMPLE VIII

One mole of laboratory grade oleic acid (99% pure) was mixed with $6.7 \times 10^{-4}$ moles of insoluble blood derivative (chlorohaemin) in a container. The contents of the container were exposed to the air and allowed to autoxidize at room temperature for a period of 2 days. The oxidation product was formulated in the following proportions: product, 0.3% by weight; and binder (mineral oil), 99.7% by weight. The formulation was bioassayed in accordance with test procedure "T" outlined above.

The results of the bioassay are set forth in Table I below. Readings were taken at the intervals given in the table. The percent of leaves browsed are given in tabular form for each of the readings. The percent of treated leaves browsed is given first followed by the percent of untreated control leaves browsed, e.g., the first data in Table 1 is "38/73," which indicates that 38% of the treated leaves were browsed as contrasted with 73% of the untreated control leaves. The same format is also used for all ensuing tables.

EXAMPLE IX

The procedure of Example VIII was repeated, substituting hemoglobin for the chlorohaemin. The results of the bioassay are set forth in Table I. The bioassay results of Examples VIII and IX illustrate that the blood catalyzed oxidation of laboratory grade oleic acid enhances the repellent effect of the repellent-producing ingredient.

EXAMPLE X

The procedure of Example VIII is repeated except that the blood catalyzed oxidation of the oleic acid is allowed to continue for 8 days prior to formulation. The results of the bioassay are set forth in Table I.

EXAMPLE XI

The procedure of Example IX is repeated, except that the hemoglobin catalyzed oxidation is allowed to continue for 8 days prior to formulation. The results of the bioassay are set forth in Table I. The bioassay results indicate that blood catalyzed oxidation of oleic acid over a longer period of time further enhances the repellent effect of the repellent-producing ingredient.

EXAMPLE XII

Laboratory grade aldehydes having from 7 to 10 carbon atoms, including heptanal, octanal, nonanal, 2-decen-1-al, and decanal were formulated with a carrier and were bioassayed in accordance with test procedure "T" outlined above. (The 2-decen-1-al ws synthesized by first preparing 4-chloro-2 cis-buten-1-ol according to the procedure outlined in *Bull. Soc. Chim. Fr.*, 1955, pp. 953–5, and reacting this intermediate with a Grignard reagent, hexyl magnesium bromide, to form 2-decen-1-ol, the alcohol corresponding to the desired aldehyde. The alcohol was then oxidized to the aldehyde using the Sarett reagent (a chromium trioxide-pyridine complex.) Each of the aldehydes were formulated in the following proportions: aldehyde, 0.3% by weight, and binder (a mixture of 15% by weight "Raeco" binder, identified above, and 85% by weight hexane), 99.7% by weight. In addition, a mixture of these aldehydes (hereafter the "$C_7$–$C_{10}$ aldehydes") was formulated with a binder in the following proportions: heptanal, 0.3% by weight, octanal, 0.3% by weight, nonanal, 0.3% by weight, decanal, 0.3% by weight; and binder (a mixture of 15% by weight Raeco and 85% by weight hexane), 98.8% by weight. The formulation containing the $C_7$–$C_{10}$ aldehydes was also bioassayed. The results of thebioassays are set forth in Table II. The results of the bioassays show a very high repellent activity in each of the aldehydes.

EXAMPLE XIII

Several aldehydes, including isobutyraldehyde, hexanal, decanal, undecanal, dodecanal and furfural, were formulated with a binder and bioassayed. Each of the aldehydes were formulated in the following proportions: aldehyde, 0.3% by weight; and binder ("Raeco"), 99.7% weight. The formulations were bioassayed in accordance with test procedure "T" above. The results of the bioassays are set forth below in Table III. The results of the bioassay show the efficiency of the aldehydes as a ruminant repellent.

EXAMPLE XIV

Laboratory grade linoleic acid (99% pure) was formulated with a carrier in the following proportions: linoleic acid, 0.3% by weight; and binder (mineral oil), 99.7% by weight. The linoleic acid was bioassayed in accordance with the test procedure "T" outlined above. The bioassay results are set forth in Table IV.

EXAMPLE XV

The procedure of Example XIV is repeated, except that prior to formulation the linoleic acid is placed in an open beaker exposed to the air under a mercury arc lamp at room temperatures for 17 hours, during which time the linoleic acid is continuously stirred. The ultraviolet light from the lamp catalyzed oxidation of the linoleic acid. The oxidation product was then formulated and bioassayed as in the Example XIV. The results of the bioassay are set forth in Table IV.

EXAMPLE XVI

Glyceryl trioleate, UCAR-180 and water were mixed in the following respective amounts: 1.5g.; 20g.; and 78.5g. The glyceryl trioleate was a commerical grade material purchased from K and K Laboratories, Inc. of Plainview, N.Y. This formulation was bioassayed in accordance with test procedure "T" oulined above. The results of the bioassay are set forth in Table V below.

EXAMPLE XVII

The procedure of Example XVI was repeated substituting glyceryl dioleate for the glyceryl trioleate. The results of the bioassay are set forth in Table V below.

EXAMPLE XVIII

The procedure of Example XVI was repeated substituting glyceryl monooleate from the glyceryl trioleate. The bioassay results are set forth in Table V below.

TABLE I

BIOASSAY RESULTS
(Examples VIII through XI)

| FORMULATION OF | PERCENT BROWSED (TREATED/CONTROL) | | | | | |
|---|---|---|---|---|---|---|
| | 2 hr. | 4 hr. | 6 hr. | 7 hr. | 9 hr. | 11 hr. |
| EX. VIII | 38/73 | 45/78 | 58/93 | — | 88/100 | 100/100 |
| EX. IX | 58/75 | 60/75 | 73/75 | — | 88/100 | 100/100 |
| EX. X | 30/73 | 30/73 | 35/73 | 53/100 | — | 100/100 |
| EX. XI | 0/88 | 8/90 | 50/95 | 75/100 | — | 100/100 |

TABLE II

BIOASSAY RESULTS
(Example XII)

| FORMULATION WITH REPELLENT INGREDIENT | PERCENT BROWSED (TREATED/CONTROL) | | | |
|---|---|---|---|---|
| | 2 hr. | 4 hr. | 6 hr. | 21 hr. |
| Heptanal | 0/60 | 8/88 | 33/90 | 98/100 |
| Octanal | 15/48 | 30/93 | 43/93 | 100/100 |
| Nonanal | 0/0 | 20/100 | 35/100 | 100/100 |
| 2-decen-1-al | 0/55 | 5/83 | 5/85 | 98/100 |
| Decanal | 0/53 | 5/83 | 5/88 | 100/100 |
| $C_7$-$C_{10}$ aldehydes | 0/10 | 3/45 | 28/58 | 100/100 |

TABLE III

BIOASSAY RESULTS
(Example XIII)

| FORMULATION WITH REPELLENT INGREDIENT | PERCENT BROWSED (TREATED/CONTROL) | | | |
|---|---|---|---|---|
| | 2 hr. | 4 hr. | 6 hr. | 21 hr. |
| Isobutyraldehyde | 0/100 | 0/100 | 0/100 | 70/100 |
| Hexanal | 0/98 | 0/98 | 5/100 | 28/100 |
| Decanal | 0/80 | 0/80 | 0/100 | 65/100 |
| Undecanal | 0/95 | 0/98 | 0/100 | 50/100 |
| Dedecanal | 0/100 | 0/100 | 0/100 | 50/100 |
| Furfural | 0/100 | 0/100 | 3/100 | 73/100 |

TABLE IV

BIOASSAY RESULTS
Examples XIV through XVII)

| FORMULATION OF | PERCENT BROWSED (TREATED/CONTROL) | | | | | |
|---|---|---|---|---|---|---|
| | 3 hr. | 6 hr. | 9 hr. | 15 hr. | 30 hr. | 39 hr. |
| EX. XIV | 0/28 | 23/63 | 35/48 | 68/95 | 73/95 | 100/100 |
| EX. XV | 0/3 | 0/13 | 13/40 | 13/68 | 20/68 | 100/100 |

TABLE V

BIOASSAY RESULTS
(Examples XVI through XVIII)

| FORMULATION OF | PERCENT BROWSED (TREATED/CONTROL) | | | | |
|---|---|---|---|---|---|
| | 1 day | 2 days | 3 days | 4 days | 6 days |
| EX. XVI | 0/100 | 0/100 | 10/100 | 100/100 | 100/100 |
| EX. XVII | 0/100 | 0/100 | 0/100 | 100/100 | 100/100 |
| EX. XVIII | 0/80 | 10/100 | 10/100 | 50/100 | 50/100 |

The present invention has been disclosed in relation to a class of repellent compositions that are applied to edible material in the form of an active ingredient, the aldehydes, or in the form of a repellent-producing oxidation precursor of the aldehydes. When applied to edible material in the effective amounts set forth above, these compositions will discourage ruminants from browsing the edible material. Although the invention has been set forth in terms of most preferred embodiments, and broader classes of repellent and repellent-producing compositions, it will be apparent to one of ordinary skill in the art after reading the foregoing specification that various changes and substitutions of equivalents can be made without departing from the scope or intent of the invention. It is therefore intended that the present invention be limited only by the definition contained in the appended claims.

What is claimed is:

1. A method for discouraging ruminants from browsing on leaves normally eaten by said ruminants comprising applying a mixture of a repellent-producing amount of an ingredient comprising oleic acid or an alkali metal, alkaline earth metal or ammonium salt of oleic acid and a repellent-producing amount of an additional ruminant repellent to leaves normally eaten by ruminants in a nonphytotoxic amount effective to discourage browsing of said leaves by said ruminants.

2. The method of claim 1 wherein said ingredient is a potassium or sodium salt of oleic acid.

3. A method for discouraging ruminants from browsing on leaves normally eaten by said ruminants comprising:
applying to said leaves a nonphytotoxic amount of a repellent-producing composition effective to discourage browsing of said leaves by said ruminants, said repellent-producing composition containing as the principal active repellent-producing ingredient a compound having the formula

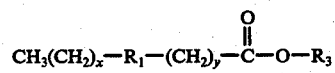

wherein:
$x$ is 5 through 7, inclusive,
$y$ is 5 through 7, inclusive,
$R_1$ is —CH=CH— or —CH=CH—CH=CH—
$R_1$ having at least one cis carbon-carbon double bond, and
$R_3$ is hydrogen, an alkali metal, an alkaline earth metal, ammonium, or an alkyl group having from one to six carbon atoms, or mixtures thereof.

4. The method of claim 3 wherein said repellent-producing ingredient is oleic acid, linoleic acid, linolenic acid or mixtures thereof.

5. The method of claim 3 wherein said compound has the formula

wherein $R_8$ is hydrogen, an alkali metal, an alkaline earth metal, or ammonium, and wherein the carbon-carbon double bond is a cis bond.

6. A method for discouraging ruminants from browsing on leaves normally eaten by said ruminants comprising:
applying to said leaves a nonphytotoxic amount of a repellent-producing composition effective to discourage browsing of said leaves by said ruminants, said repellent-producing composition containing as the principal active repellent-producing ingredient a compound having the formula

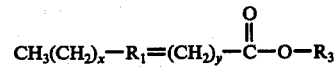

wherein:
$x$ is 5 through 7, inclusive,
$y$ is 5 through 7, inclusive,
$R_1$ is —CH=CH— or —CH=CH—CH=CH—, $R_1$ having at least one cis carbon-carbon double bond, and $R_3$ is a relatively inert group that will allow said ingredient to undergo autoxidation at or adjacent the unsaturated bonds of $R_1$ after application to said leaves.

7. The method of claim 6 wherein $R_3$ is hydrogen, an alkali or alkaline earth metal, ammonium, an alkyl group having from one to six carbon atoms, or mixtures thereof.

8. The method of claim 6 wherein $R_3$ is diacyloxypropyl selected from 1,2-diacyloxypropyl or 1,3-diacyloxypropyl, acyloxypropyl selected from 1-acyloxy-2-hydroxypropyl or 2-acyloxy-1-hydroxypropyl, or dihydroxypropyl selected from 1,2-dihydroxypropyl or 1,3-dihydroxypropyl, and wherein the acyl group is derived from a linear aliphatic carboxylic acid having from 14 to 20 carbon atoms.

* * * * *

UNITED STATES PATENT OFFICE
CERTIFICATE OF CORRECTION

PATENT NO. : 4,065,576
DATED : December 27, 1977
INVENTOR(S) : KATASHI OITA et al.

It is certified that error appears in the above-identified patent and that said Letters Patent are hereby corrected as shown below:

In column 4, line 36, "prevnt" should read --prevent--;

in column 6, line 14, the dark dot at the end of the line should be deleted;

in column 6, line 57, "the", second occurrence, should read --this--;

in column 9, line 11, "Hass" should read --Haas--; and in column 10, line 10, "reference" should read --referenced--.

Signed and Sealed this

Thirteenth Day of June 1978

[SEAL]

Attest:

RUTH C. MASON
Attesting Officer

DONALD W. BANNER
Commissioner of Patents and Trademarks